Sept. 20, 1932. L. F. LAMBERT Plant Pat. 27
MUSHROOM
Filed Nov. 7, 1930
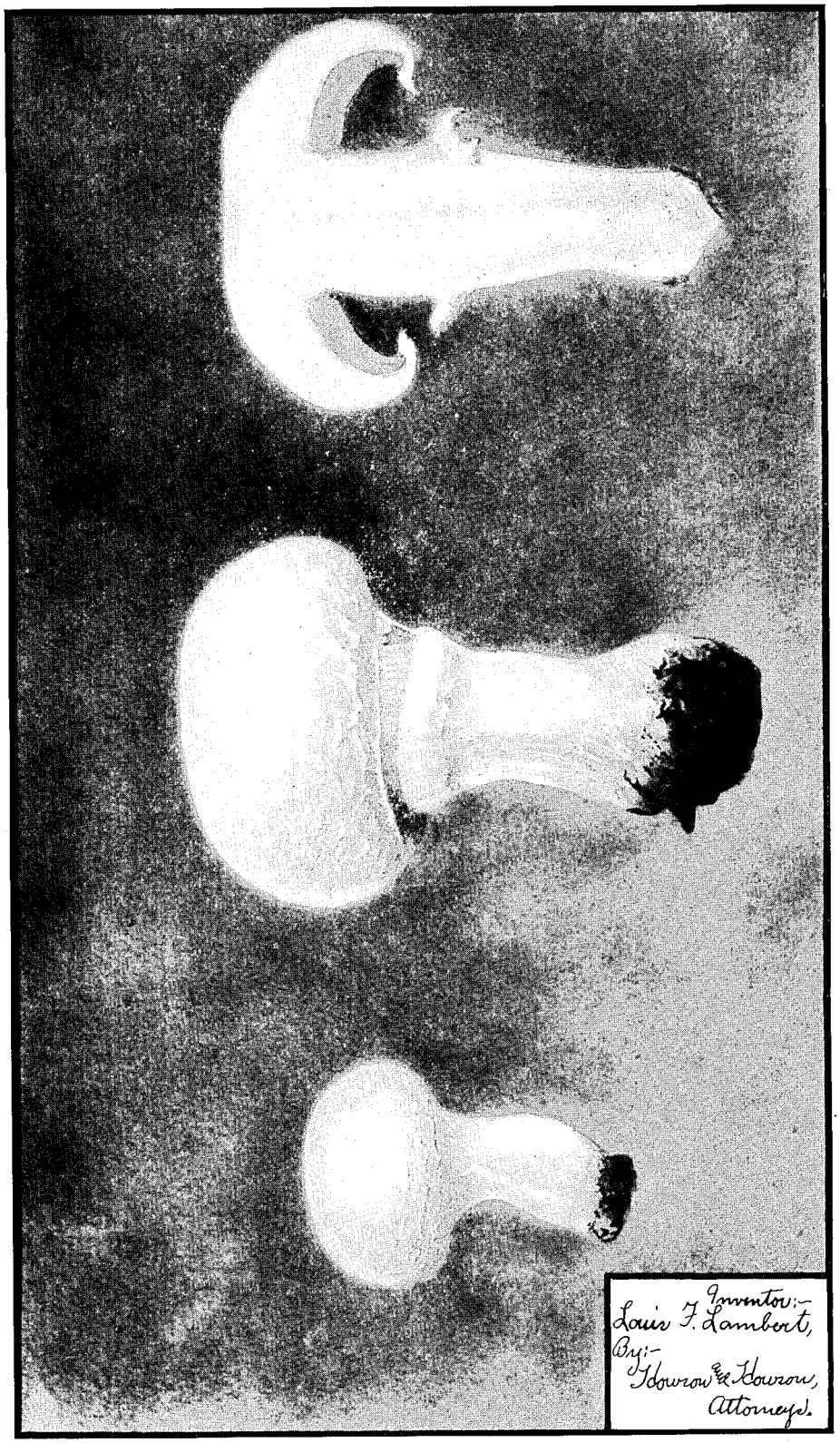

Patented Sept. 20, 1932

Plant Pat. 27

UNITED STATES PATENT OFFICE

LOUIS F. LAMBERT, OF COATESVILLE, PENNSYLVANIA

MUSHROOM

Application filed November 7, 1930. Serial No. 494,116.

My new mushroom has a cap which is white with pale buff or golden scales thereon, and of greater depth than any white mushroom known to me. It is characterized commercially by the fact that both the mushroom and mycelium or spawn develop more rapidly than any white mushroom with which I am familiar and by the fact that it is more prolific than any other white variety.

The accompanying drawing illustrates several forms of the mushroom. The following is a botanical description of the mushroom, color references being to the Maerz and Paul Dictionary of Color 1930: Agaricus campestris variety:

Cap: When veil breaks, 4.5 to 10.5 cm. wide, flattened-hemispherical, center slightly depressed, white, with well-defined rather broad appressedly-floccose scales (these about 3 mm. broad), colored 11 C 5 (when plants are exposed to draught) to 10 B 2, to 10 between A and B 1; the shading on inflexed border 10 between A and B 3; margin strongly and persistently incurved and exceeding the gills 2 to 5 mm., and thickened. Width of flesh 4 to 10 cm. Color of flesh white, discoloring upon bruising to slightly creamy and brownish.

Gills: Colored 12 A 5 to 12 A 7; breadth 2.5 to 3.5 mm., close, free and unequal; spore-print color 8 L 12.

Stem: Up to 6 cm. long and 1.8 cm. thick, equal to slightly enlarged in the middle. Base usually provided with a slight bulb, white, floccose-scaly, the scales pointing upward, staining to 12 G 7 and slightly pinker, stuffed.

Ring median: Flaring, double, outer ring stellately split and quickly retracting; margin of ring lacerated.

Remarks: Stem above ring silky and with a pinkish luster. The double ring has the two parts closely applied.

Spores: Elliptical to broadly ovate, 5 to 6 by 6 to 8 $\mu$.

I claim:

A mushroom as shown and described characterized by a white cap with floccose scales oxidizing to a pale buff or golden tint.

LOUIS F. LAMBERT.